United States Patent
You et al.

(10) Patent No.: US 11,447,761 B2
(45) Date of Patent: Sep. 20, 2022

(54) XYLANASE MUTANT AND ITS PREPARATION METHOD AND APPLICATION

(71) Applicant: Jiangsu University Of Science And Technology, Zhenjiang (CN)

(72) Inventors: Shuai You, Zhenjiang (CN); Wenxin Zhang, Huai'an (CN); Ziqian Cha, Liancheng Town (CN); Chen Xie, Rugao (CN); Yan Ge, Changzhou (CN); Yanghao Hu, Chengdu (CN); Jun Wang, Zhenjiang (CN)

(73) Assignee: JIANGSU UNIVERSITY OF SCIENCE AND TECHNOLOGY, Zhenjiang (CN)

( * ) Notice: Subject to any disclaimer, the term of this patent is extended or adjusted under 35 U.S.C. 154(b) by 0 days.

(21) Appl. No.: 17/219,550

(22) Filed: Mar. 31, 2021

(65) Prior Publication Data
US 2022/0251527 A1    Aug. 11, 2022

(30) Foreign Application Priority Data

Feb. 7, 2021   (CN) .......................... 202110178825.2

(51) Int. Cl.
| | |
|---|---|
| *C12N 9/24* | (2006.01) |
| *A23K 20/189* | (2016.01) |
| *C12P 19/14* | (2006.01) |

(52) U.S. Cl.
CPC ............ *C12N 9/248* (2013.01); *A23K 20/189* (2016.05); *C12P 19/14* (2013.01)

(58) Field of Classification Search
CPC ........ C12N 9/248; A23K 20/189; C12P 19/14
See application file for complete search history.

(56) References Cited

PUBLICATIONS

Sadowski et al., The sequence-structure relationship and protein function prediction. Current Opinion in Structural Biology, 2009, vol. 19: 357-362. (Year: 2009).*

Seffernick et al., Melamine deaminase and Atrazine chlorohydrolase: 98 percent identical but functionally different. J. Bacteriol., 2001, vol. 183 (8): 2405-2410. (Year: 2001).*

Tang et al., Identification of Dehalobacter reductive dehydrogenases that catalyse dechlorination of chloroform, 1,1,1-richloroethane and 1,1-dichloroethane. Phil Trans R Soc B, 2013, vol. 368: 20120318, pp. 1-10. (Year: 2013).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

* cited by examiner

*Primary Examiner* — Ganapathirama Raghu
(74) *Attorney, Agent, or Firm* — WPAT, PC (57) ABSTRACT

The present invention discloses a kind of xylanase mutant and its preparation method and application, which relates to the technical field of genomic engineering and genetic engineering. Such mutant includes one or more mutants obtained by taking xylanase HwXy110A as female parent to conduct saturation mutagenesis to the site of Gly363. Specifically, relates to obtaining 19 mutants through site-directed mutagenesis, and then conducting yeast expression to them, after that, obtaining two mutants with significantly improved specific activity and thermal stability through screening of thermal stability and catalytic activity; the present invention can significantly improve the thermal stability and catalytic efficiency of xylanase through modifying the site of Gly363, and is of important guiding significance for improving the thermal stability and the catalytic efficiency of the 10th family of xylanases and other glycoside hydrolases as well as lays the foundation for its application in industrial production.

11 Claims, 3 Drawing Sheets

Specification includes a Sequence Listing.

SEQUENCE LISTING

<160> NUMBER OF SEQ ID NOS: 8

<210> SEQ ID NO 1
<211> LENGTH: 1203
<212> TYPE: DNA

<213> ORGANISM: Artificial Sequence
<220> FEATURE:
<223> OTHER INFORMATION: Xylanase Mutant

<400> SEQUENCE: 1

```
actaagaccg aaacctccgt tcaaatgatg accgaaacct ctaccgttac ccaatctgcc      60
tcttgctctg gattgtctgg atccaccatg acctccggag gaaacggatc taccatgtct     120
accaccatgt cttcttcttc cagaactaga ccatctacta ccttgaccgc cactgctact     180
gctaccggtt ccggtttgaa cgatgccgcc gaagatgctg gaaagcttta ctttggtact     240
gccgccgata ttccaggtac tggagaagct caagacccat actacatgag agaatttaat     300
aacactcacg atttcggaca agctactcca gctaatatta tgaagtttgt ttacaccgaa     360
ccagaacaag gtgtttttaa ttttactggt ggagactact ttttgaacat tactgaccca     420
accagaact acatcagatg tcataacctt gtttggggtt cccaattgcc aacttggatt     480
actaacccat ccactaactg gactaacgct actttgtctg ctgctttgca caatcatgtt     540
tacactaccg tttcatattt cggtgataag tgttttgcct gggatgttgt taacgagggt     600
ttgtctgata acccagctgg ttcttatatg gagaacattt ggtacaacgt cattggtcct     660
gaatacattc ctatggcttt tgctgctgct caacaggcta ttgaagataa tgatttgtct     720
gttaagttgt actacaacga ttacaacatt gagtacttgg gtaacaagtc tttggctgct     780
caggacattg ttactgagtt gaaaggtaga ggtattcaaa ttgatggagt tggtttggag     840
agtcatttca ttgccggttc tactccatct caatctgctc aagaagataa catgagagca     900
tttgttaatt tgggtgttga agttgccgtt accgaattgg atgttagatt gaacttgcca     960
ccaaacgcca ctactgaggc ccaacaaaaa ttggattact acaacaccgt tgcagcttgt    1020
gttgctgttg atggttgtgt tggaattacc gtttgggatt ttgttgatac ttactcttgg    1080
atcccaggaa cctttccagg tcaaggatat ggtgatttgt ttttgcagcc tgatggtgct    1140
gatactcctt tgttgaagaa ggctgcttat gatggttgtt tggaagcttt ggaaggtgaa    1200
taa                                                                  1203
```

<210> SEQ ID NO 2
<211> LENGTH: 400
<212> TYPE: PRT
<213> ORGANISM: Artificial Sequence
<220> FEATURE:
<223> OTHER INFORMATION: Xylanase Mutant

<400> SEQUENCE: 2

```
Thr Lys Thr Glu Thr Ser Val Gln Met Met Thr Glu Thr Ser Thr Val
1               5                  10                  15

Thr Gln Ser Ala Ser Cys Ser Gly Leu Ser Gly Ser Thr Met Thr Ser
            20                  25                  30

Gly Gly Asn Gly Ser Thr Met Ser Thr Thr Met Ser Ser Ser Ser Arg
        35                  40                  45

Thr Arg Pro Ser Thr Thr Leu Thr Ala Thr Ala Thr Ala Thr Gly Ser
    50                  55                  60

Gly Leu Asn Asp Ala Ala Glu Asp Ala Gly Lys Leu Tyr Phe Gly Thr
65                  70                  75                  80

Ala Ala Asp Ile Pro Gly Thr Gly Glu Ala Gln Asp Pro Tyr Tyr Met
                85                  90                  95

Arg Glu Phe Asn Asn Thr His Asp Phe Gly Gln Ala Pro Ala Asn
            100                 105                 110
```

```
Ile Met Lys Phe Val Tyr Thr Glu Pro Glu Gln Gly Val Phe Asn Phe
            115                 120                 125

Thr Gly Gly Asp Tyr Phe Leu Asn Ile Thr Asp Pro Thr Lys Asn Tyr
    130                 135                 140

Ile Arg Cys His Asn Leu Val Trp Gly Ser Gln Leu Pro Thr Trp Ile
145                 150                 155                 160

Thr Asn Pro Ser Thr Asn Trp Thr Asn Ala Thr Leu Ser Ala Ala Leu
                165                 170                 175

His Asn His Val Tyr Thr Thr Val Ser Tyr Phe Gly Asp Lys Cys Phe
            180                 185                 190

Ala Trp Asp Val Val Asn Glu Gly Leu Ser Asp Asn Pro Ala Gly Ser
            195                 200                 205

Tyr Met Glu Asn Ile Trp Tyr Asn Val Ile Gly Pro Glu Tyr Ile Pro
    210                 215                 220

Met Ala Phe Ala Ala Ala Gln Gln Ala Ile Glu Asp Asn Asp Leu Ser
225                 230                 235                 240

Val Lys Leu Tyr Tyr Asn Asp Tyr Asn Ile Glu Tyr Leu Gly Asn Lys
                245                 250                 255

Ser Leu Ala Ala Gln Asp Ile Val Thr Glu Leu Lys Gly Arg Gly Ile
            260                 265                 270

Gln Ile Asp Gly Val Gly Leu Glu Ser His Phe Ile Ala Gly Ser Thr
            275                 280                 285

Pro Ser Gln Ser Ala Gln Glu Asp Asn Met Arg Ala Phe Val Asn Leu
            290                 295                 300

Gly Val Glu Val Ala Val Thr Glu Leu Asp Val Arg Leu Asn Leu Pro
305                 310                 315                 320

Pro Asn Ala Thr Thr Glu Ala Gln Gln Lys Leu Asp Tyr Tyr Asn Thr
                325                 330                 335

Val Ala Ala Cys Val Ala Val Asp Gly Cys Val Gly Ile Thr Val Trp
            340                 345                 350

Asp Phe Val Asp Thr Tyr Ser Trp Ile Pro Gly Thr Phe Pro Gly Gln
            355                 360                 365

Gly Tyr Gly Asp Leu Phe Leu Gln Pro Asp Gly Ala Asp Thr Pro Leu
    370                 375                 380

Leu Lys Lys Ala Ala Tyr Asp Gly Cys Leu Glu Ala Leu Glu Gly Glu
385                 390                 395                 400
```

<210> SEQ ID NO 3
<211> LENGTH: 1200
<212> TYPE: DNA
<213> ORGANISM: Artificial Sequence
<220> FEATURE:
<223> OTHER INFORMATION: Xylanase Mutant

<400> SEQUENCE: 3

```
actaagaccg aaacctccgt tcaaatgatg accgaaacct ctaccgttac ccaatctgcc      60
tcttgctctg gattgtctgg atccaccatg acctccggag aaacggatc taccatgtct     120 accaccatgt cttcttcttc cagaactaga ccatctacta ccttgaccgc cactgctact     180
gctaccggtt ccggttttgaa cgatgccgcc gaagatgctg aaagctttta ctttggtact     240
gccgccgata ttccaggtac tggagaagct caagacccat actacatgag agaatttaat     300
aacactcacg atttcggaca agctactcca gctaatatta tgaagtttgt ttacaccgaa     360
ccagaacaag gtgttttttaa ttttactggt ggagactact ttttgaacat tactgaccca     420
accaagaact acatcagatg tcataacctt gtttggggtt cccaattgcc aacttggatt     480
```

-continued

```
actaacccat ccactaactg gactaacgct actttgtctg ctgctttgca caatcatgtt    540
tacactaccg tttcatattt cggtgataag tgttttgcct gggatgttgt taacgagggt    600
ttgtctgata acccagctgg ttcttatatg gagaacattt ggtacaacgt cattggtcct    660
gaatacattc ctatggcttt tgctgctgct caacaggcta ttgaagataa tgatttgtct    720
gttaagttgt actacaacga ttacaacatt gagtacttgg gtaacaagtc tttggctgct    780
caggacattg ttactgagtt gaaaggtaga ggtattcaaa tgatggagt tggtttggag    840 agtcatttca ttgccggttc tactccatct caatctgctc aagaagataa catgagagca    900
tttgttaatt tgggtgttga agttgccgtt accgaattgg atgttagatt gaacttgcca    960
ccaaacgcca ctactgaggc ccaacaaaaa ttggattact acaacaccgt gcagcttgt   1020 gttgctgttg atggttgtgt tggaattacc gtttgggatt tgttgatac ttactcttgg   1080 atcccacgta cctttccagg tcaaggatat ggtgatttgt ttttgcagcc tgatggtgct   1140
gatactcctt tgttgaagaa ggctgcttat gatggttgtt tggaagcttt ggaaggtgaa   1200
```

<210> SEQ ID NO 4
<211> LENGTH: 400
<212> TYPE: PRT
<213> ORGANISM: Artificial Sequence
<220> FEATURE:
<223> OTHER INFORMATION: Xylanase Mutant

<400> SEQUENCE: 4

```
Thr Lys Thr Glu Thr Ser Val Gln Met Met Thr Glu Thr Ser Thr Val
1               5                   10                  15

Thr Gln Ser Ala Ser Cys Ser Gly Leu Ser Gly Ser Thr Met Thr Ser
            20                  25                  30

Gly Gly Asn Gly Ser Thr Met Thr Thr Met Ser Ser Ser Ser Arg
        35                  40                  45

Thr Arg Pro Ser Thr Thr Leu Thr Ala Thr Ala Thr Ala Thr Gly Ser
    50                  55                  60

Gly Leu Asn Asp Ala Ala Glu Asp Ala Gly Lys Leu Tyr Phe Gly Thr
65                  70                  75                  80

Ala Ala Asp Ile Pro Gly Thr Gly Glu Ala Gln Asp Pro Tyr Tyr Met
                85                  90                  95

Arg Glu Phe Asn Asn Thr His Asp Phe Gly Gln Ala Thr Pro Ala Asn
            100                 105                 110

Ile Met Lys Phe Val Tyr Thr Glu Pro Glu Gln Gly Val Phe Asn Phe
        115                 120                 125

Thr Gly Gly Asp Tyr Phe Leu Asn Ile Thr Asp Pro Thr Lys Asn Tyr
    130                 135                 140

Ile Arg Cys His Asn Leu Val Trp Gly Ser Gln Leu Pro Thr Trp Ile
145                 150                 155                 160

Thr Asn Pro Ser Thr Asn Trp Thr Asn Ala Thr Leu Ser Ala Ala Leu
                165                 170                 175

His Asn His Val Tyr Thr Thr Val Ser Tyr Phe Gly Asp Lys Cys Phe
            180                 185                 190

Ala Trp Asp Val Val Asn Glu Gly Leu Ser Asp Asn Pro Ala Gly Ser
        195                 200                 205

Tyr Met Glu Asn Ile Trp Tyr Asn Val Ile Gly Pro Glu Tyr Ile Pro
    210                 215                 220

Met Ala Phe Ala Ala Ala Gln Gln Ala Ile Glu Asp Asn Asp Leu Ser
225                 230                 235                 240
```

```
Val Lys Leu Tyr Tyr Asn Asp Tyr Asn Ile Glu Tyr Leu Gly Asn Lys
                245                 250                 255

Ser Leu Ala Ala Gln Asp Ile Val Thr Glu Leu Lys Gly Arg Gly Ile
            260                 265                 270

Gln Ile Asp Gly Val Gly Leu Glu Ser His Phe Ile Ala Gly Ser Thr
        275                 280                 285

Pro Ser Gln Ser Ala Gln Glu Asp Asn Met Arg Ala Phe Val Asn Leu
    290                 295                 300

Gly Val Glu Val Ala Val Thr Glu Leu Asp Val Arg Leu Asn Leu Pro
305                 310                 315                 320

Pro Asn Ala Thr Thr Glu Ala Gln Gln Lys Leu Asp Tyr Tyr Asn Thr
                325                 330                 335

Val Ala Ala Cys Val Ala Val Asp Gly Cys Val Gly Ile Thr Val Trp
            340                 345                 350

Asp Phe Val Asp Thr Tyr Ser Trp Ile Pro Arg Thr Phe Pro Gly Gln
        355                 360                 365

Gly Tyr Gly Asp Leu Phe Leu Gln Pro Asp Gly Ala Asp Thr Pro Leu
    370                 375                 380

Leu Lys Lys Ala Ala Tyr Asp Gly Cys Leu Glu Ala Leu Glu Gly Glu
385                 390                 395                 400
```

<210> SEQ ID NO 5
<211> LENGTH: 1200
<212> TYPE: DNA
<213> ORGANISM: Artificial Sequence
<220> FEATURE:
<223> OTHER INFORMATION: Xylanase Mutant

<400> SEQUENCE: 5

```
actaagaccg aaacctccgt tcaaatgatg accgaaacct ctaccgttac ccaatctgcc    60
tcttgctctg gattgtctgg atccaccatg acctccggag aaacggatc taccatgtct    120
accaccatgt cttcttcttc cagaactaga ccatctacta ccttgaccgc cactgctact   180
gctaccggtt ccggtttgaa cgatgccgcc gaagatgctg aaagcttta ctttggtact    240
gccgccgata ttccaggtac tggagaagct caagacccat actacatgag agaatttaat   300
aacactcacg atttcggaca agctactcca gctaatatta tgaagtttgt ttacaccgaa   360
ccagaacaag gtgtttttaa ttttactggt ggagactact ttttgaacat tactgaccca   420
accaagaact acatcagatg tcataacctt gtttggggtt cccaattgcc aacttggatt   480
actaacccat ccactaactg gactaacgct actttgtctg ctgctttgca caatcatgtt   540
tacactaccg tttcatattt cggtgataag tgttttgcct gggatgttgt taacgagggt   600
ttgtctgata acccagctgg ttcttatatg gagaacattt ggtacaacgt cattggtcct   660
gaatacattc ctatggcttt tgctgctgct caacaggcta ttgaagataa tgatttgtct   720
gttaagttgt actacaacga ttacaacatt gagtacttgg gtaacaagtc tttggctgct   780
caggacattg ttactgagtt gaaaggtaga ggtattcaaa ttgatggagt tggtttggag   840
agtcatttca ttgccggttc tactccatct caatctgctc aagaagataa catgagagca   900
tttgttaatt tgggtgttga agttgccgtt accgaattgg atgttagatt gaacttgcca   960
ccaaacgcca ctactgaggc ccaacaaaaa ttggattact acaacaccgt tgcagcttgt   1020
gttgctgttg atggttgtgt tggaattacc gtttgggatt ttgttgatac ttactcttgg  1080
atcccaaaga cctttccagg tcaaggatat ggtgatttgt ttttgcagcc tgatggtgct  1140
```
gatactcctt tgttgaagaa ggctgcttat gatggttgtt tggaagcttt ggaaggtgaa   1200

<210> SEQ ID NO 6
<211> LENGTH: 400
<212> TYPE: PRT
<213> ORGANISM: Artificial Sequence
<220> FEATURE:
<223> OTHER INFORMATION: Xylanase Mutant

<400> SEQUENCE: 6

Thr Lys Thr Glu Thr Ser Val Gln Met Met Thr Glu Thr Ser Thr Val
1               5                   10                  15

Thr Gln Ser Ala Ser Cys Ser Gly Leu Ser Gly Ser Thr Met Thr Ser
            20                  25                  30

Gly Gly Asn Gly Ser Thr Met Ser Thr Thr Met Ser Ser Ser Ser Arg
        35                  40                  45

Thr Arg Pro Ser Thr Thr Leu Thr Ala Thr Ala Thr Ala Thr Gly Ser
    50                  55                  60

Gly Leu Asn Asp Ala Ala Glu Asp Ala Gly Lys Leu Tyr Phe Gly Thr
65                  70                  75                  80

Ala Ala Asp Ile Pro Gly Thr Gly Glu Ala Gln Asp Pro Tyr Tyr Met
                85                  90                  95

Arg Glu Phe Asn Asn Thr His Asp Phe Gly Gln Ala Thr Pro Ala Asn
            100                 105                 110

Ile Met Lys Phe Val Tyr Thr Glu Pro Gln Gly Val Phe Asn Phe
        115                 120                 125

Thr Gly Gly Asp Tyr Phe Leu Asn Ile Thr Asp Pro Thr Lys Asn Tyr
130                 135                 140

Ile Arg Cys His Asn Leu Val Trp Gly Ser Gln Leu Pro Thr Trp Ile
145                 150                 155                 160

Thr Asn Pro Ser Thr Asn Trp Thr Asn Ala Thr Leu Ser Ala Ala Leu
                165                 170                 175

His Asn His Val Tyr Thr Thr Val Ser Tyr Phe Gly Asp Lys Cys Phe
            180                 185                 190

Ala Trp Asp Val Val Asn Glu Gly Leu Ser Asp Asn Pro Ala Gly Ser
        195                 200                 205

Tyr Met Glu Asn Ile Trp Tyr Asn Val Ile Gly Pro Glu Tyr Ile Pro
    210                 215                 220

Met Ala Phe Ala Ala Ala Gln Gln Ala Ile Glu Asp Asn Asp Leu Ser
225                 230                 235                 240

Val Lys Leu Tyr Tyr Asn Asp Tyr Asn Ile Glu Tyr Leu Gly Asn Lys
                245                 250                 255

Ser Leu Ala Ala Gln Asp Ile Val Thr Glu Leu Lys Gly Arg Gly Ile
            260                 265                 270

Gln Ile Asp Gly Val Gly Leu Glu Ser His Phe Ile Ala Gly Ser Thr
        275                 280                 285

Pro Ser Gln Ser Ala Gln Glu Asp Asn Met Arg Ala Phe Val Asn Leu
    290                 295                 300

Gly Val Glu Val Ala Val Thr Glu Leu Asp Val Arg Leu Asn Leu Pro
305                 310                 315                 320

Pro Asn Ala Thr Thr Glu Ala Gln Gln Lys Leu Asp Tyr Tyr Asn Thr
                325                 330                 335

Val Ala Ala Cys Val Ala Val Asp Gly Cys Val Gly Ile Thr Val Trp
            340                 345                 350

Asp Phe Val Asp Thr Tyr Ser Trp Ile Pro Lys Thr Phe Pro Gly Gln

-continued

```
                355                 360                 365
Gly Tyr Gly Asp Leu Phe Leu Gln Pro Asp Gly Ala Asp Thr Pro Leu
    370                 375                 380

Leu Lys Lys Ala Ala Tyr Asp Gly Cys Leu Glu Ala Leu Glu Gly Glu
385                 390                 395                 400

<210> SEQ ID NO 7
<211> LENGTH: 27
<212> TYPE: DNA
<213> ORGANISM: Artificial Sequence
<220> FEATURE:
<223> OTHER INFORMATION: Primer for amino acid residue saturation
      mutagenesis
<220> FEATURE:
<221> NAME/KEY: misc_feature
<222> LOCATION: (1)..(3)
<223> OTHER INFORMATION: n is a, c, g, or t

<400> SEQUENCE: 7
nnntgggatc caagagtaag tatcaac                                         27

<210> SEQ ID NO 8
<211> LENGTH: 27
<212> TYPE: DNA
<213> ORGANISM: Artificial Sequence
<220> FEATURE:
<223> OTHER INFORMATION: Primer for amino acid residue saturation
      mutagenesis
<220> FEATURE:
<221> NAME/KEY: misc_feature
<222> LOCATION: (13)..(15)
<223> OTHER INFORMATION: n is a, c, g, or t

<400> SEQUENCE: 8
tcttggatcc cannnacctt tccaggt                                         27
```

XYLANASE MUTANT AND ITS PREPARATION METHOD AND APPLICATION

FIELD OF THE INVENTION

The present invention relates to the technical field of genomic engineering and genetic engineering, specifically involves a kind of xylanase mutant and its preparation method and application, wherein, particularly relates to a kind of xylanase mutant with high specific activity and heat resistance and its preparation method and application.

Statement Regarding Sequence Listing

The sequence listing associated with this application is provided in text format in lieu of a paper copy and is hereby incorporated by reference into the specification. The name of the text file containing the sequence listing is updatedSL. The text file is 15619 bytes; was created on Jul. 18, 2022; contains no new matter; and is being submitted electronically via EFS-Web.

BACKGROUND OF THE INVENTION

There are more than 50% of the biomasses existed in nature are composed of cellulose, hemicellulose, lignin and pectin, etc. Xylan is one of the main components of hemicellulose, which is a renewable resource second only to cellulose in the aspect of content in nature, accounting for about ⅓ of renewable organic carbon on the earth. The structure of xylan is relatively complex, and the backbone of which is made up of xylopyranose through being connected by β-D-1,4-xylosidic bonds, as well as the compositions of side chain are diverse, mainly consist of ferulic acid and α-L-arabinofuranose residue, 0-acetyl, coumaric acid and glucuronic acid residue, etc. Therefore, the hydrolysis of xylan requires the participation of multiple enzymes.

Xylanase is a key enzyme for the hydrolysis of xylan, which can cleave the β-1,4-glycosidic bond of the backbone of xylan, and thus produce small oligosaccharides or monosaccharides. Xylan can be used widely, including in such industries as animal feed, food, papermaking, beer brewing and green energy, etc. Xylanase is distributed in 11 glycoside hydrolase families (GH) including GHS, GH7, GH8, GH10, GH11, GH16, GH26, GH30, GH43, GH52, and GH62, wherein, the xylanases of GH10 and GH11 families are studied mostly. The xylanases of GH10 family belongs to the (β/α)8-barrel structure, and their molecular weights are higher than those of the xylanases of GH11 family, as well as with strong stability and a broad substrate spectrum. Most of the xylanases of GH10 family derived from microorganisms show the greatest activity in the neutral or slightly acidic environment at medium temperature (about 40° C. to 60° C.). However, in industrial applications, most of the application environments are high temperature environment, thus, obtaining xylanase with excellent thermal stability and high catalytic activity is vital to industrial production. Up to now, there are 53 crystal structures of xylanases derived from funguses have been analyzed, which have laid the foundation for improving the properties of xylanases.

Nowadays, protein engineering is widely used in the improvement of enzyme molecules, which means, changing the structure of protein molecule through altering or modifying genes or the protein itself, and thus realizing the modification of enzyme functions. Protein engineering is mainly used to design and modify enzymatic properties such as thermal stability, catalytic efficiency, substrate specificity and extreme environmental tolerance. It mainly involves such methods as directed evolution, rational design and semi-rational design. Wherein, rational design refers to a fast and effective means of modification, which requires more accuracy of protein molecular structure. The common methods adopted by rational design mainly include module replacement and site-directed mutagenesis. For instance, the thermal stability and the pH stability of the xylanase XynA derived from *Thermoascus aurantiacus* can be significantly improved through this method. In addition, the site-saturation mutagenesis is an effective modification method of rational design. More precisely, such method can screen out the amino acid sites closely related to enzyme functions through simulating computation by computer, and then conduct saturation mutagenesis at this site so that fully develop the functional potential of the key amino acid sites, and thus obtain mutants with improved properties. As a result, finding a way to obtain more kinds of xylanase mutants with superior performance to enrich the species of xylanases of the glycoside hydrolase family and satisfy the needs of different industrial fields is an urgent problem need to be solved.

SUMMARY OF THE INVENTION

The purpose of the present invention is to provide a kind of xylanase mutant and its preparation method and application, and thus address the above-mentioned problems existed in the prior art. The present invention can obtain mutants through screening after the saturation mutagenesis of the key amino acid site of Gly363 of the xylanase the 10th family HwXy110A. To be specific, it obtains two xylanase mutants with significantly improved thermal stability and catalytic efficiency, and thus can be used widely in industries of feed or sugar production through degrading xylan by utilizing biomass.

In order to achieve above-mentioned purposes, the present invention provides following scheme:

The present invention provides a kind of xylanase mutant with high specific activity and heat resistance, which consists of one or more mutants obtained by taking xylanase HwXy110A as female parent to conduct saturation mutagenesis to the site of Gly363.

Preferably, obtains two xylanase mutants with high specific activity and heat resistance, i.e., HwXy110A_G363R and HwXy110A_G363K after taking xylanase HwXy110A as female parent to conduct saturation mutagenesis to the site of Gly363.

Preferably, the amino acid sequence of the said HwXy110A_G363R is as shown in SEQ ID NO: 4;

The said amino acid sequence of the HwXy110A_G363K is as shown in SEQ ID NO:6. The present invention also provides nucleotide sequence of the said xylanase mutant with high specific activity and heat resistance described through coding.

Preferably, it has a nucleotide sequence as shown in SEQ ID NO: 3 or SEQ ID NO: 5.

The present invention also provides a kind of recombinant vector, and the said recombinant vector consists of the said nucleotide sequence according to claim 4.

The present invention also provides a kind of recombinant strain, which consists of the said recombinant vector or integrating the said nucleotide sequence into the genome of the said recombinant strain.

The present invention also provides a preparation method for the said xylanase mutant with high specific activity and heat resistance, which consists of following steps:

Step 1: Obtain the nucleotide sequence of the xylanase mutant with high specific activity and heat resistance, and after amplification, transform the amplified products into DMT competent cells, and thus obtain the recombinant expression vector of xylan mutant;

Step 2: Transform the obtained recombinant expression vector of xylan mutant into *Pichia pastoris*, and then induce expression, and thus obtain the recombinant strain of *Pichia pastoris*;

Step 3: Ferment and cultivate the recombinant strain of *Pichia pastoris* to induce the expression of recombinant xylanase;

Step 4: Recover and purify the xylanase mutant with high specific activity and heat resistance.

Preferably, the said *Pichia pastoris* is *Pichia pastoris* GS115.

The present invention also provides an application of the said xylanase mutant with high specific activity and heat resistance in industries of feed or sugar production through degrading xylan by utilizing biomass.

The present invention discloses following technical effects:

The present invention can one or more mutants obtained by taking xylanase HwXyl10A, which is a xylanase gene derived from *Hortaea werneckii*, as female parent to conduct saturation mutagenesis to the site of Gly363. To be specific, it can screen out two mutants with significantly improved specific activity and thermal stability, i.e., HwXyl10A_G363R and HwXyl10A_G363K, based upon constructing a recombinant strain containing such mutant and after induction and cultivation. In the aspect of thermal stability, the half-time (t½) of the mutants, i.e., HwXyl10A_G363R and HwXyl10A_G363K at the temperature of 80° C. are 15 min and 20 min, respectively, which are 1.9 times and 2.5 times of that of the wild-type enzyme HwXyl10A (8 min); in addition, the T50 values of mutants, i.e., HwXyl10A_G363R and HwXyl10A_G363K are 78° C. and 80° C., respectively, which have been increased by 3° C. and 5° C. than that of the wild-type enzyme HwXyl10A (75° C.); in terms of catalytic activity, the specific activities of mutants, i.e., HwXyl10A_G363R and HwXyl10A_G363K are 4030 U/mg and 4990 U/mg, which have been increased by 24% and 53%, respectively based upon comparing with the wild-type HwXyl10A (3260U/mg); meanwhile, the optimum pH value and optimum temperature are basically the same as those of the wild-type HwXyl10A, which fully satisfy the requirements of feed production and degradation of biomass. Compared to such approaches as aimlessly screening of bacteria or artificial (natural) mutagenesis, the modification of enzyme molecules reduced the time for modification of enzyme properties. Thus, the xylanase mutant with high specific activity and heat resistance of the present invention can be widely used in industries of feed additives or sugar production through degrading xylan by utilizing biomass.

BRIEF DESCRIPTION OF THE FIGURES

For the purpose of illustrating the embodiments of the present invention or the technical scheme in the prior art more clearly, the text below will briefly introduce the drawings required in the embodiments. It is obvious that the drawings described below are only certain embodiments of the present invention. For those of ordinary skill in the art, other drawings can be obtained based on these drawings without paying creative labor.

DESCRIPTION OF THE INVENTION

Various exemplary embodiments of the present invention will be described in detail herein. It should be noted that such detailed description cannot be deemed as a limitation to the present invention, but should be understood as a more detailed description related to certain aspects, characteristics, and embodiments of the present invention.

It should be understood that the terms described in the present invention are only used to describe specific embodiments rather than imposing restriction on the present invention. In addition, for the numerical range referred to in the present invention, it should be understood that it discloses each intermediate value between the upper limit and the lower limit of the range specifically. Furthermore, each smaller range between the intermediate value within any stated values or stated range and the intermediate value within any other stated values or stated range is also included in the present invention. The upper limits and the lower limits of these smaller ranges can be independently included or excluded from the range.

Unless otherwise specified, all technical and scientific terms used herein have the same meaning as those commonly understood by those of ordinary skill in the art of the present invention. Although the present invention only describes the preferred methods and materials, any methods and materials similar or equivalent to those described herein can also be used in the implementation or testing of the present invention. All bibliographies referred to in this specification are incorporated by reference, which are used to disclose and describe the methods and/or materials related to the mentioned bibliographies. In the event of conflict with any incorporated bibliographies, the contents of this specification shall prevail.

It is obvious to those of ordinary skill in the art that various improvements and variations can be made to the specific embodiments of the specification described herein without departing from the scope or spirit of the present invention. Furthermore, other embodiments obtained from the specification of the present invention are also obvious to those of ordinary skill in the art. And the specification and examples of this application are only exemplary.

For those words of "consist of", "include", "have", and "contain", etc. used herein are all open terms, which means including but not limited to.

Unless otherwise specified, the reagents or materials used in the following embodiments can be obtained through commercial channels.

The test materials used in the following embodiments:

1. Strains and vectors: the expression host, i.e., *Pichia pastoris* GS115 is purchased from Invitrogen.

2. Enzymes and other biochemical reagents: the high-fidelity polymerase is purchased from Fermentas, and the xylan of beech is purchased from Sigma. Others are domestic analytical reagents (all of which can be purchased from general biochemical reagent companies).

3. Mediums:
1) The YPD medium: contains 2% of glucose, 2% of peptone and 1% of yeast extract;
2) LB medium: contains 1% of peptone, 0.5% of yeast extract, 1% of NaCl and 1% of agar powder (solid);
3) MD medium: contains 1.5% of agarose, 2% of glucose, 0.00004% of Biotin and 1.34% of YNB;
5) BMGY medium: contains 2% of peptone, 1% of yeast extract, 1% of glycerine (V/V), 0.00004% of Biotin and 1.34% of YNB;
6) BMMY medium: contains 2% of peptone, 1% of yeast extract, 1.34% of YNB, 0.5% methanol (V/V), and 0.00004% of Biotin.

Embodiment 1. The Obtaining of the Coding Gene of the Xylanase Mutant with High Specific Activity and Heat Resistance Taking the recombinant expression vector, i.e., pic9r-HwXy 110a, of the gene of xylanase HwXyl10a derived from *Hortaea werneckii* (the nucleotide sequence is as shown in SEQ ID NO: 1 and the amino acid sequence is as shown in SEQ ID NO: 2) as template, and then adopt the method of site-directed mutagenesis to conduct saturation mutagenesis to the site of Gly363, wherein, the primer design is as shown in Table 1. In addition, the bibliography related to the mutating method and the cloning method is (Improvement in catalytic activity and thermostability of a GH10 xylanase and its synergistic degradation of biomass with cellulase; You, et al., 2019).

TABLE 1

Primers for saturation mutagenesis to the site of Gly363 in xylanase HwXyl10A

| | Primers | Sequences (5'→3') [a] | Size (bp) |
|---|---|---|---|
| SEQ ID NO: 7 | Gly363-PF | nnntgggatccaagagtaagtatcaac | 27 |
| SEQ ID NO: 8 | Gly363-PR | tatggatcccannnacctttccaggt | 27 |

Embodiment 2. The Preparation of the Xylanase Mutant with High Specific Activity and Heat Resistance Transforming the linear recombinant expression vector obtained by PCR of the embodiment 1 directly into the competence of DMT, and then verify the bacterial colony of PCR, and thus obtain the nucleotide sequences of 19 mutants of this site except Gly, after that, transform them into *Pichia pastoris* GS115 after the linearization of recombinant plasmids, and thus obtain the recombinant yeast strain GS115/HwXy110A-G363X (wherein, X represents 19 amino acids except Gly).

Inoculating the strain of GS115 which contains recombinant plasmids into a 10 mL test tube with 2 mL of BMGY medium, and then cultivate it in a shaker at the temperature of 30° C. and at the rotational speed of 220 rpm for 48 hours, after that, centrifuge 3000 g of culture solution for 5 minutes, and then discard the supernatant and conduct sedimentation, after that, take 2 mL of BMMY medium containing 0.5% methanol to resuspend and complete induction and cultivation at the temperature of 30° C. and at the rotational speed of 220 rpm for 48 h. After that, take the supernatant to conduct enzyme activity detection, and thus screen out the mutants with improved thermal stability and the catalytic activity based upon comparing with the wild-type enzyme, i.e., HwXyl10A_G363R (the amino acid sequence of which is as shown in SEQ ID NO: 4, and the nucleotide sequence is as shown in SEQ ID NO: 3) and HwXyl10A_G363K (the amino acid sequence of which is as shown in SEQ ID NO: 6 and the nucleotide sequence is as shown in SEQ ID NO: 5).

Figure 1:
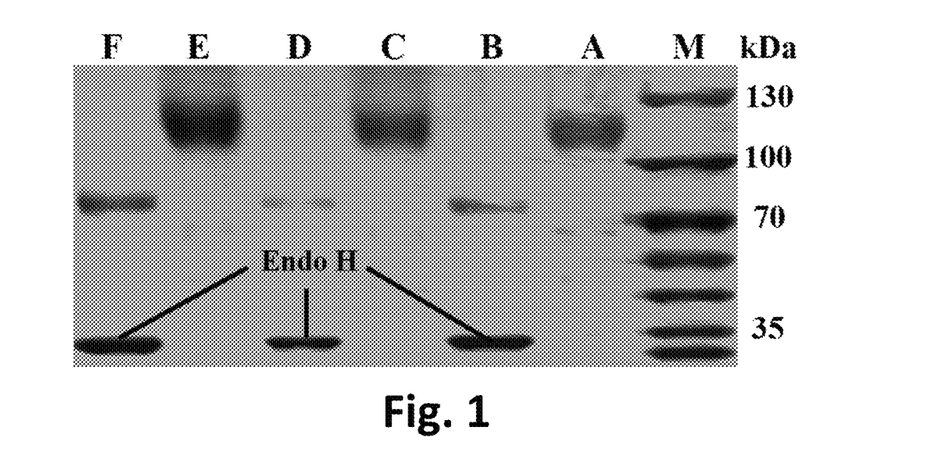
FIG. 1 shows the SDS-PAGE analysis of the xylanase mutant with high specific activity and heat resistance, wherein M represents the low molecular weight protein Marker; A, C and E represent the purified wild-type enzyme HwXyl10A, and the mutants, i.e., HwXyl10A_G363R and HwXyl10A_G363K; and B, D and F are HwXyl10A, HwXyl10A_G363R and HwXyl10A_G363K after de-N glycosylation respectively.

Amplifying the fermentation system of the wild-type GS115/HwXyl10A and the two mutants, i.e., GS115/HwXyl10A_G363R and GS115/HwXy 110A_G363K, wherein, inoculate them into the YPD medium to obtain culture solution of seed firstly, i.e., inoculate into a 1 L erlenmeyer flask with 300 mL BMGY medium according to the inoculum size of 1%, and then cultivate it in a shaker at the temperature of 30° C. and at the rotational speed of 220 rpm for 48 hours, after that, centrifuge 3000 g of culture solution for 5 minutes, and then discard the supernatant and conduct sedimentation, after that, take 100 mL of BMMY medium containing 0.5% methanol to resuspend and complete induction and cultivation at the temperature of 30° C. and at the rotational speed of 220 rpm. During the process, add 0.5 mL of methanol every 12 hours to keep the methanol concentration of the bacterial solution at 0.5%, meanwhile, take the supernatant to conduct enzyme activity detection. Finally, concentrate the supernatant to 20 mL, and purify the protein by anion exchange method to conduct measurement and comparison of enzymatic properties. After purifying the expressed xylanase, its protein content can account for more than 90% of the total protein (as shown in FIG. 1).

Embodiment 3. The Comparative Analysis of Enzymatic Properties of the Recombinant Xylanase Mutant with High Specific Activity and Heat Resistance and the Wild-Type Xylanase Mutant 1. Measurement through DNS method The specific method is as follows: according to the optimum pH and at the optimum temperature of each, the reaction system of 1 mL of solution consists of taking 100 μL diluted enzyme solution and 900 μL of substrate, and then, reacting for 10 min, as well as adding 1.5 mL DNS to stop the reaction, after that, boiling for 5 min with boiling water. Then, measuring the OD value of 540 nm after cooling. Wherein, one unit of enzyme activity (U) is defined as the amount of enzyme required to decompose xylan, and thus produce 1 μmoL of reducing sugar per minute under the given conditions.

2. The measurement of properties of the recombinant xylanase mutant with high specific activity and heat resistance and the wild-type xylanase mutant (1) The measurement method for the optimal pH value and the pH stability of the recombinant xylanase mutant with high specific activity and heat resistance and the wild-type xylanase mutant Completing enzymatic reaction on the purified xylanase mutant obtained in the embodiment 2 and the wild-type xylanase at different pH values (2.0-7.0), and thus measure their optimal pH values. In addition, the measurement of Xylanase activity of substrate xylan is completed at the temperature of 75° C. in 0.1 mol/L of buffer solution of citric acid-disodium hydrogen phosphate with different pH values (2.0, 2.5, 3, 3.5, 4, 4.5, 5, 5.5, 6, 6.5, 7.0).

Figure 2:
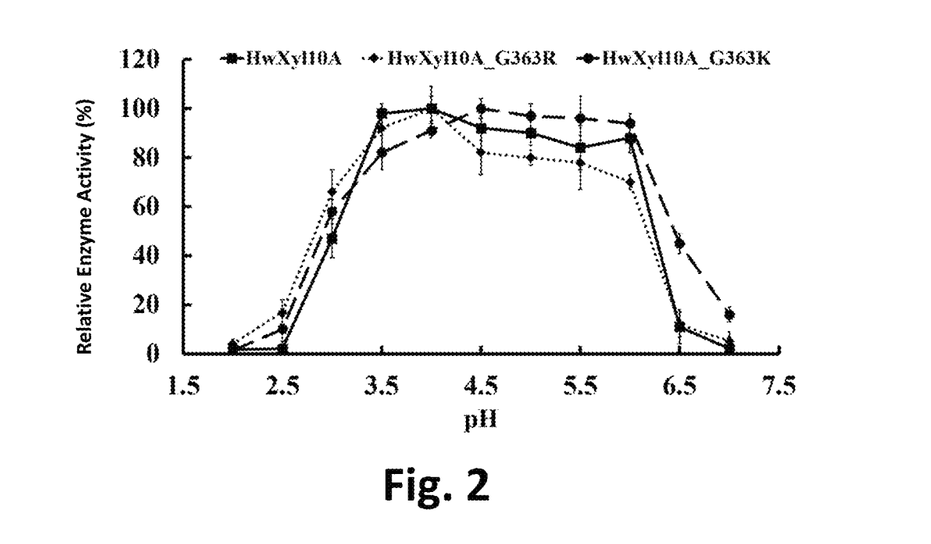
FIG. 2 shows the measurement results of optimal pH values of the wild-type xylanase and two xylanase mutants, i.e., HwXyl10A_G363R and HwXyl10A_G363K.
Figure 3:
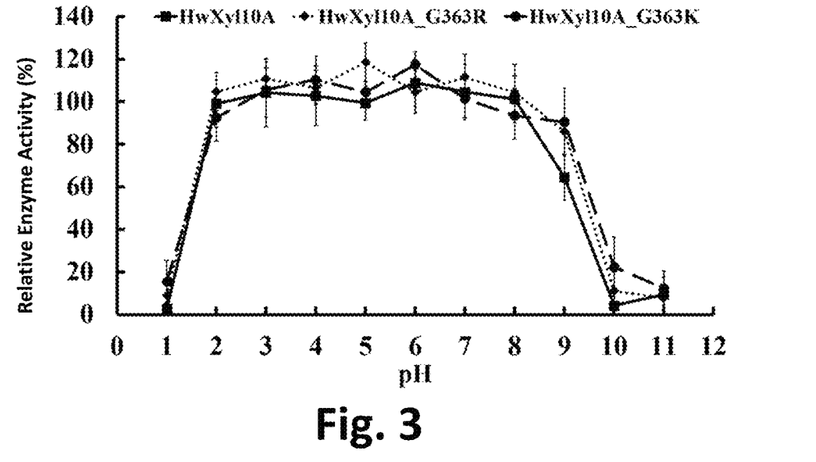
FIG. 3 shows the measurement results of pH stability of the wild-type xylanase and two mutants, i.e., HwXyl10A_G363R and HwXyl10A_G363K.

The results are as shown in FIG. 2, the optimal reaction pH values of the wild-type xylanase and the xylanase mutants are approximate and are between 4.0-4.5; wherein, the remaining enzyme activity of the wild-type xylanase and the xylanase mutants are measured after being processed at the pH values of 1.0-12.0 and at the treatment of 37° C. for 1 hour, and the results are as shown in FIG. 3, wherein, the pH stability of the wild-type xylanase is not significantly different from that of the two xylanase mutants, which stays between pH2.0-pH9.0 stably.

(2) The measurement method for the optimum temperatures of the wild-type xylanase and the xylanase mutants The measurement of optimal temperatures of the recombinant xylanase mutant with high specific activity and heat resistance and the wild-type xylanase is as follows: complete enzymatic reaction in the buffer solution system of 0.1 mol/L citric acid-disodium hydrogen phosphate buffer solution (pH 4.5) and at different temperatures (35-90° C.).

Figure 4:
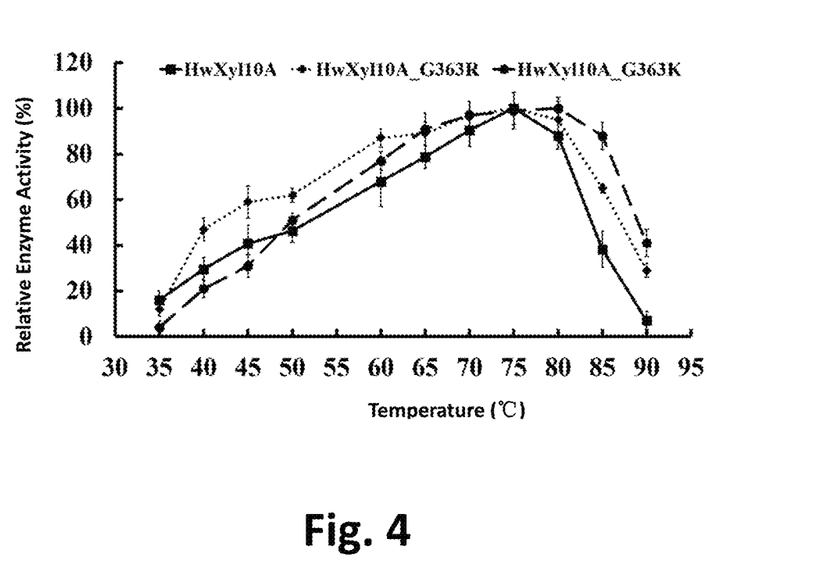
FIG. 4 shows the measurement results of optimal temperatures of the wild-type xylanase and two mutants, i.e., HwXyl10A_G363R and HwXyl10A_G363K.

The results are as shown in FIG. 4, which indicate that the optimal temperatures of the recombinant xylanase mutant with high specific activity and heat resistance and the wild-type xylanase (75° C.) are between 75° C. and 80° C., and the relative enzyme activity of two mutants is significantly increased based upon comparing with that of the wild-type enzyme at the high temperature of 80-90° C.

(3) The measurement method for the thermal stability of the wild-type xylanase and the mutants The half-time (t½) at the temperature of 80° C.: The remaining enzyme activity of the mutants and the wild-type xylanase are measured after being treated at the temperature of 80° C. for different times, which is up to 30 minutes.

Figure 5:
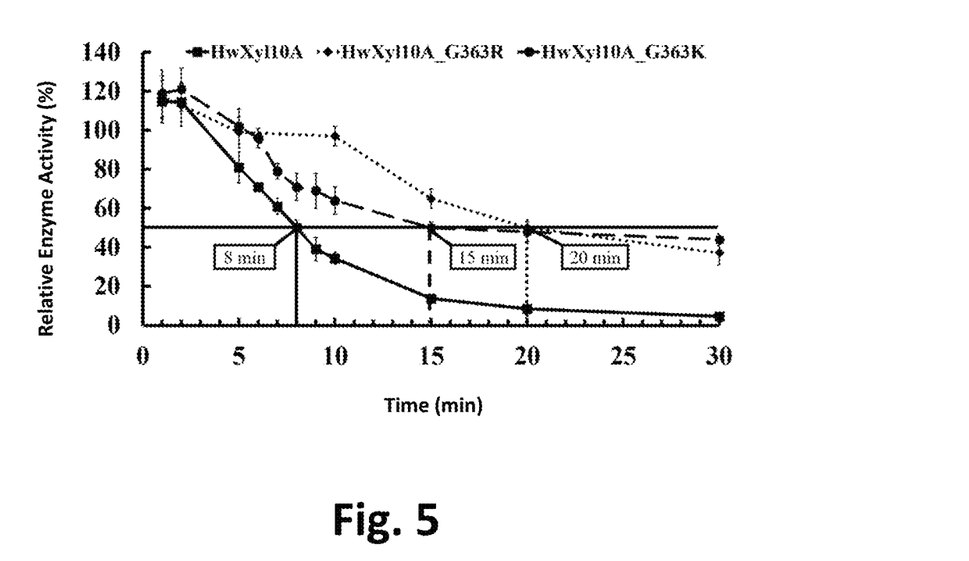
FIG. 5 shows the measurement results of half-time (t½) of the wild-type xylanase and two mutants, i.e., HwXyl10A_G363R and HwXyl10A_G363K at the temperature of 80° C.

The measurement results of the half-time at the temperature of 80° C. are as shown in FIG. 5, which indicate that the t½ of the xylanase mutants HwXyl10A_G363R and HwXyl10A_G363K are 15 minutes and 20 minutes, respectively, which have been extended 0.88 times and 1.5 times than that of the wild-type xylanase (8 minutes), respectively, and the mutant HwXyl10A_G363K shows the best thermal stability.

T50: The xylanase mutant and the wild-type xylanase are treated at the temperature between 60° C. and 85° C. for half an hour, and the corresponding temperature when the enzyme activity remains half of the original represents the T50 value of the enzyme.

Figure 6:
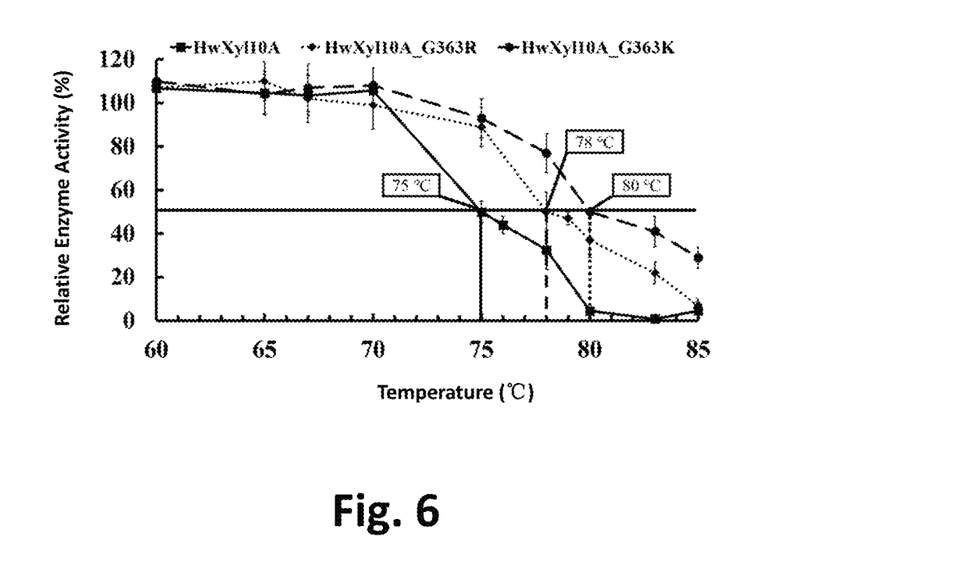
FIG. 6 shows the measurement results of T50 values of the wild-type xylanase and two mutants, i.e., HwXyl10A_G363R and HwXyl10A_G363K.

The measurement results of T50 are as shown in FIG. 6, which indicate that the T50 values of the xylanase mutants HwXyl10A_G363R and HwXyl10A_G363K are 78° C. and 80° C., respectively, which have been increased by 3° C. and 5° C. than that of the wild-type xylanase HwXyl10A (75° C.), respectively. Such results are consistent with the trend of measurement results of half-time. And the sequence of thermal stability is: HwXyl10A_G363K>HwXyl10A_G363R>HwXyl10A.

(4) The measurement method for the kinetic parameters of the recombinant xylanase mutant with high specific activity and heat resistance and the wild-type xylanase The measurement method refers to the bibliography of (A thermophilic and acid stable family-10 xylanase from the acidophilic fungus Bispora sp MEY-1. Extremophiles. 2009; 13:849-57. Luo, et al., 2009), which is used to measure the time of first-order reaction. In addition, the reaction time for measuring Km and Vmax is determined as 5 minutes. Furthermore, xylans with different concentrations (i.e., 1.25, 1.0, 0.8, 0.4, 0.2, 0.15 and 0.1 mg/mL) will be used as the substrate, and the enzyme activity will be measured under the optimal conditions (i.e., at the optimal temperature and pH value), and then calculate corresponding reaction rate, and thus figure out the $K_m$ value and the $V_{max}$ by means of the GraFit7 software.

The catalytic efficiency ($k_{cat}/K_m$) of the recombinant xylanase mutants with high specific activity and heat resistance under respective optimal conditions and taking xylan as the substrate is 3050 mL/s·mg and 3180 mL/s·mg, respectively, which has been increased by 3% and 7% than that of the wild-type xylanase (2970 mL/s·mg), respectively. And the specific activities of the recombinant xylanase mutants with high specific activity and heat resistance are 4030 U/mg and 4990 U/mg, respectively, which have been increased by 24% and 53% than that of the wild-type xylanase (U/mg) (see Table 2).

TABLE 2

The comparison table of the specific activity and the kinetic parameters between the xylanase mutants with high catalytic efficiency and the wild-type xylanase mutant

|  | $K_m$ (mg/mL) | $k_{cat}$ ($s^{-1}$) | $k_{cat}/K_m$ (mL/s · mg) | specific activity (U/mg) |
|---|---|---|---|---|
| HwXyl10A | 0.88 ± 0.13 | 2610 ± 74 | 2970 ± 383 | 3260 ± 62 |
| HwXyl10A_G363R | 0.98 ± 0.11 | 2990 ± 104 | 3050 ± 119 | 4030 ± 177 |
| HwXyl10A_G363K | 1.13 ± 0.07 | 3590 ± 176 | 3180 ± 159 | 4990 ± 201 |

The above-mentioned embodiments only describe the preferred approaches of the present invention rather than imposing restriction on the scope of the present invention. Various variations and improvements of the technical scheme of the present invention made by those of ordinary skill in the art without departing from the design spirit of the present invention should fall within the protection scope determined by the claims of the present invention.

The invention claimed is:

1. A xylanase mutant comprising:
one or more mutants obtained by using xylanase HwXy110A as a template to complete amino acid residue Gly363 site-saturation mutagenesis;
wherein the xylanase HwXy110A is encoded by the xylanase gene HwXy110a obtained from *Hortaea werneckii*, the nucleotide sequence of the xylanase gene is SEQ ID NO: 1, and the amino acid sequence of the xylanase HwXy110A is SEQ ID NO: 2.

2. The xylanase mutant according to claim 1, wherein the one or more mutants comprise: a mutant HwXy110A_G363R and a mutant HwXy110A_G363K.

3. The xylanase mutant according to claim 2, wherein the amino acid sequence of the mutant HwXy101A_G363R is SEQ ID NO: 4; and
the amino acid sequence of the mutant HwXy110A_G363K is SEQ ID NO:6.

4. A nucleotide sequence of the xylanase mutant according to claim 1.

5. The nucleotide sequence according to claim 4, comprising: the nucleotide sequence is SEQ ID NO: 3 or SEQ ID NO: 5.

6. A recombinant vector, wherein the recombinant vector comprising: the nucleotide sequence according to claim 4.

7. A recombinant strain, comprising: the recombinant vector according to claim 6.

8. A recombinant strain, wherein the nucleotide sequence according to claim 5 is integrated into a genome of the recombinant strain.

9. A preparation method for the xylanase mutant according to claim 1, comprising:
step 1: obtaining a nucleotide sequence of the xylanase mutant, and after amplification, transforming amplified products into dimethyltryptamine (DMT) competent cells, and thus obtaining a recombinant expression vector of the xylanase mutant;
step 2: transforming the obtained recombinant expression vector of the xylanase mutant into *Pichia pastoris*, and then inducing expression, and thus obtaining a recombinant strain of *Pichia pastoris*;
step 3: fermenting and cultivating the recombinant strain of *Pichia pastoris* to induce an expression of recombinant xylanase; and
step 4: recovering and purifying the xylanase mutant.

10. The preparation method for the xylanase mutant according to claim 9, wherein the *Pichia pastoris* is *Pichia pastoris* GS115.

11. A method of a use of the xylanase mutant according to claim 1 in producing feed or producing sugar through degrading xylan by utilizing biomass.

* * * * *